US008471294B2

(12) United States Patent
Garcia et al.

(10) Patent No.: US 8,471,294 B2
(45) Date of Patent: Jun. 25, 2013

(54) GAN-BASED NITRIC OXIDE SENSORS AND METHODS OF MAKING AND USING THE SAME

(75) Inventors: Michael A. Garcia, Durham, NC (US); Scott D. Wolter, Durham, NC (US); April S. Brown, Durham, NC (US); Joseph Bonaventura, Durham, NC (US); Thomas F. Kuech, Madison, WI (US)

(73) Assignee: Duke University, Durham, NC (US)

( * ) Notice: Subject to any disclaimer, the term of this patent is extended or adjusted under 35 U.S.C. 154(b) by 0 days.

(21) Appl. No.: 12/948,946

(22) Filed: Nov. 18, 2010

(65) Prior Publication Data

US 2011/0097837 A1  Apr. 28, 2011

Related U.S. Application Data

(62) Division of application No. 11/937,375, filed on Nov. 8, 2007, now Pat. No. 7,868,354.

(60) Provisional application No. 60/857,502, filed on Nov. 8, 2006.

(51) Int. Cl.
*H01L 29/66* (2006.01)

(52) U.S. Cl.
USPC ............ 257/192; 257/253; 257/E29.216; 438/116

(58) Field of Classification Search
USPC ............ 257/253, 192, E29.216; 436/116
See application file for complete search history.

(56) References Cited

U.S. PATENT DOCUMENTS

| 5,603,820 A | 2/1997 | Malinski et al. |
| 6,433,356 B1 | 8/2002 | Cahen et al. |
| 6,647,796 B2 | 11/2003 | Beach et al. |
| 7,361,946 B2 * | 4/2008 | Johnson et al. ............... 257/253 |

(Continued)

OTHER PUBLICATIONS

Addison, A.W. et al., "Hemoglobin: autoreduction and spectroscopy," Biochem. (1986) 25:4104-4113.

(Continued)

*Primary Examiner* — Kenneth Parker
*Assistant Examiner* — Dale E Page
(74) *Attorney, Agent, or Firm* — Michael Best & Friedrich LLP

(57) ABSTRACT

GaN-based heterojunction field effect transistor (HFET) sensors are provided with engineered, functional surfaces that act as pseudo-gates, modifying the drain current upon analyte capture. In some embodiments, devices for sensing nitric oxide (NO) species in a NO-containing fluid are provided which comprise a semiconductor structure that includes a pair of separated GaN layers and an AlGaN layer interposed between and in contact with the GaN layers. Source and drain contact regions are formed on one of the GaN layers, and an exposed GaN gate region is formed between the source and drain contact regions for contact with the NO-containing fluid. The semiconductor structure most preferably is formed on a suitable substrate (e.g., SiC). An insulating layer may be provided so as to cover the semiconductor structure. The insulating layer will have a window formed therein so as to maintain exposure of the GaN gate region and thereby allow the gate region to contact the NO-containing fluid. Electrical contact pads are preferably provided in some embodiments so as to be in electrical contact with the source and drain contact regions, respectively. Electrical leads may thus be connected to the contact pads. According to other embodiments, the NO detection device will include a metalloporphyrin adsorbed on the GaN gate region.

6 Claims, 4 Drawing Sheets

Schematic of Functionalized GaN-AlGaN HFET

U.S. PATENT DOCUMENTS

| | | | |
|---|---|---|---|
| 7,868,354 | B2 | 1/2011 | Garcia et al. |
| 2003/0036054 | A1 | 2/2003 | Ladisch et al. |
| 2003/0138829 | A1 | 7/2003 | Unger et al. |
| 2004/0072360 | A1* | 4/2004 | Naaman et al. ............... 436/116 |
| 2004/0157281 | A1 | 8/2004 | Hulkower et al. |
| 2005/0097941 | A1 | 5/2005 | Sandvik et al. |
| 2006/0267570 | A1 | 11/2006 | Arkin |

OTHER PUBLICATIONS

Angelo et al., "Interaction of NO with hemoglobin: from microbes to man," Methods Enzym. (2008) 436:125-158.

Ashkenasy, G. et al., "Molecular engineering of semiconductor surfaces and devices," Acc. Chem. Res. (2002) 35:121-128.

Bayer, M. et al., "Theoretical study of electrolyte gate AlGaN/GaN field effect transistors," Appl. Phys. Lett. (2005) 97:033703, 6 pages.

Bedioui, F. et al., "Electrochemical nitric oxide sensors for biological samples—principle, selected examples and applications," Electroanalysis (2003) 15:5-18.

Cahen, D. et al., "The cooperative molecular field effect," Adv. Funct. Mater. (2005) 15:1571-1578.

Crawford, J.H. et al., "Transduction of NO-bioactvity by the red blood cell in sepsis: novel mechanisms of vasodilation during acute inflammatory disease," Blood (2004) 104:1375-1382.

Culotta, E. et al., "NO news is good news," Science (1992) 258(5090):1862-1865.

Eickhoff, M. et al., "Electronics and sensors-based on pyroelectric AlGaN/GaN heterostructures; Part B: sensor applications," Phys. Stat. Sol. (2003) 6:1908-1918.

Flechtner, K. et al., "No-induced reversible switching of the electronic interaction between a porphyrin-coordinated cobalt ion and a silver surface," J. Am. Chem. Soc. (2007) 129:12110-12111.

Garcia, M. et al., "Functionalization and characterization of InAs and InP surfaces with hemin," J. Vac. Sci. Technol. (2007) 25:1504-1510.

Garcia, M.A. et al., "Comparison of functionalized III-V semiconductor response for nitric oxide," Sensor Letters (2008) 6:627-634.

Garcia, M.A. et al., "Impact of porphyrin functional groups on InAs gas sensors," (Nov. 5, 2007) 21 pages, Retrieved from the Internet: http://nanohub.org/resources/3149/download/2007.07.19-garcia.mcw.pdf.

Gartsman, K. et al., "Molecular control of a GaAs transistor," Chem. Phys. Lett. (1998) 283(5):301-306.

Gaston, B., "Nitric oxide and thiol groups," Biochim. Biophys. Acta (1999) 1411:323-333.

Gomez, R. et al., "Instrumentation system for in vivo organ studies," IEEE (2001) 1:26-1624.

Gow, A.J. et al., "Reactions between nitric oxide and haemoglobin under physiological conditions," Nature (1998) 391:169-173.

Gow, A.J. et al., "The oxyhemoglobin reaction of nitric oxide," Proc. Natl. Acad. Sci. USA (1999) 96:9027-9032.

Haga, Y. et al., "Biomedical microsystems for minimally invasive diagnosis and treatment," Proceedings of IEEE (2004) 92:98-114.

Herold, S. et al., "Mechanistic studies of S-nitrosothiol formation by NO*/O2 and by NO*/methemoglobin," Arch. Biochem. Biophys. (2005) 436:386-396.

Hess, D.T. et al., "Protein s-nitrosylation: purview and parameters," Nat. Rev. Mol. Cell Biol. (2005) 6:150-166.

Jia et al., "S-nitrosohaemoglobin: a dynamic activity of blood involved in vascular control," Nature (1996) 380:221-226.

Kadish, K.M. et al., editors, Applications: Past, Present and Future. The Porphyrin Handbook, Academic Press: San Diego, CA (1999) vol. 6, pp. 240-250 (cover and table of contents only).

Kirchner, C. et al., "Corrosion protection and long-term chemical functionalization of gallium arsenide in an aqueous environment," Adv. Funct. Mat. (2002) 12(4):266-276.

Kruszyna, R. et la., "Nitrite conversion to nitric oxide in red cells and its stabilization as a nitrosylated valency hybrid of hemoglobin," J. Pharm. Exp. Thera. (1987) 241:307-313.

Lantoine, F. et al., "Selective and sensitive electrochemical measurement of nitric-oxide in aqueous-solution—discussion and new results," J. Electroanal. Chem. (1995) 392:85-89.

Lu, H. et al., "High temperature hall effect sensors based on AlGaN/GaN heterojunctions," J. Appl. Phys. (2006) 99:114510-1-114510-4.

Luchsinger, B.P. et al., "Assessments of the chemistry and vasodilatory activity of nitrite with hemoglobin under physiologically relevant conditions," J. Inorg. Biochem. (2005) 99:912-921.

Luchsinger, B.P. et al., "Routes to S-nitrosohemoglobin formation with heme redox and preferential reactivity in the beta subunits," Proc. Natl. Acad. Sci. USA (2003) 100:461-566.

McMahon, T.J. et al., "Extrapulmonary effects of inhaled nitrix oxide: role of reversible S-nitrosylation of erythrocytic hemoglobin," Proc. Am. Thorac. Soc. (2006) 3:153-160.

McMahon, T.J. et al., "Nitric oxide in the human respiratory cycle," Nat. Med. (2002) 8:711-717.

Moore, E.G. et al., "Cooperativitiy in the dissociation of nitric oxide from hemoglobin," J. Biol. Chem. (1976) 251:2788-2794.

Pearton, S.J. et al., "GaN-based diodes and transistors for chemical, gas, biological and pressure sensing," J. Phys. Condens. Matter (2004) 16:R961R994.

Potter, W., "Reduction of nitric oxide to nitrous oxide by cobalt porphyrins and corrins," Fuel Proces. Tech. (1994) 40:355-360.

Rovira, c. et al., "Equilibrium geometries and electronic structure of iron-porphyrin complexes: a density functional study," J. Phys. Chem. A. (1997) 101:8914-8925.

Sharma, V.S. et al., "Reaction of nitric oxide with heme proteins and model compounds of hemoglobin," Biochem. (1987) 26:3837-3843.

Sharma, V.S. et al., "The dissociation of NO from nitrosylhemoglobin," J. Biol. Chem. (1978) 253:6467-6472.

Ship, N.J. et al., "Rates of release of nitric oxide from HbSNO and internal electron transfer," Bioorg. Chem. (2003) 31:3-10.

Singel et al., "Chemical physiology of blood flow regulation by red blood cels," Annu. Rev. Physiol. (1997) 67:99-145.

Skromme, B.J. et al., "Effects of passivating ionic films on the photoluminescence properties of GaAs," Appl. Phys. Lett. (1987) 51(24):2022-2024.

Smith, R.P., "Chemicals reacting with various forms of hemoglobin: biological significance, mechanisms, and determination," J. For. Sci. (1991) 36:662-672.

Stamler et al., Blood flow regulation by S-nitrosohemoglobin in the physiological oxygen gradient, Science (1997) 276:2034-2037.

Steinhoff, G. et al., "pH response for GaN surfaces and its application for pH-sensitive field-effect transistors," Appl. Phys. Lett. (2003) 83(1):177-179.

Stutzmann, M. et al., "GaN-based heterostructures for sensor applications," Dia. Related Matt. (2002) 11:886-891.

Taketa, F. et al., "Chain nonequivalence in binding of nitric oxide to hemoglobin," J. Biol. Chem. (1978) 253:5448-5451.

Uhlrich, J. et al., "Interfacial chemistry and energy band line-up of pentacene with the GaN (0001) surface," J. Crys. Grow. (2007) 300:204-211.

Vilan, A. et al., "How organic molecules can control electronic devices," Trends in Biotech. (2002) 20:22-29.

Wolter, S.D. et al., "Porphyrination of III-V compound semiconductor surfaces for detection of exhaled breath indicators of physiological status," Keynote lecture at SMCBS' 2007 International Workshop, See online Journal of SMCBS' 2007 International Workshop, 2 pages.

Wu, D.G. et al., "Direct detection of low-concentration NO in physiological solutions by a new GaAs-based sensor," Chem. Eur. J. (2001) 7(8):1743-1749.

Zhao, Y. et al., "Thionitroxides, RSNHO: the structure of the SNO moiety in 'S-nitrosohemoglobin' a possible NO reservoir and transporter," J. Am. Chem. Soc. (2006).

United States Patent Office Action for U.S. Appl. No. 11/937,375 dated Aug. 24, 2009 (7 pages).

United States Patent Office Action for U.S. Appl. No. 11/937,375 dated Apr. 27, 2010 (8 pages).

United States Patent Office Action for U.S. Appl. No. 11/937,375 dated Jun. 17, 2010 (4 pages).

United States Patent Notice of Allowance for U.S. Appl. No. 11/937,375 dated Jul. 9, 2010 (5 pages).

International Search Report and Written Opinion for Application No. PCT/US2009/047546 dated Nov. 2, 2009 (10 pages).

Invitation to Pay Additional Fees for Application No. PCT/US2009/047546 dated Jun. 24, 2009 (2 pages).
International Search Report and Written Opinion for Application No. PCT/US2010/023917 dated Jun. 14, 2010 (17 pages).

United States Patent Office Action for U.S. Appl. No. 13/201,181 dated Oct. 19, 2012 (13 pages).

* cited by examiner

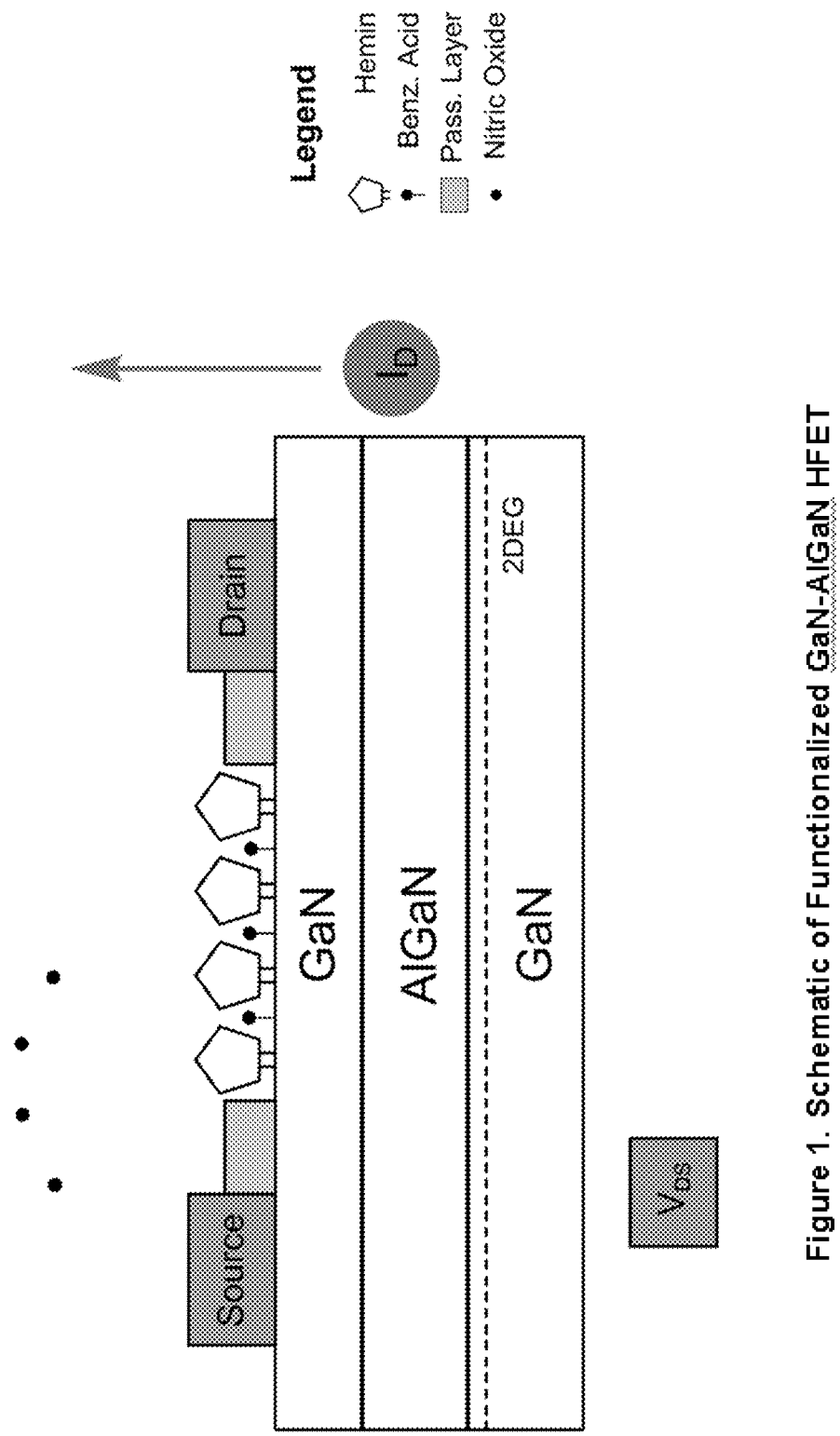
Figure 1. Schematic of Functionalized GaN-AlGaN HFET

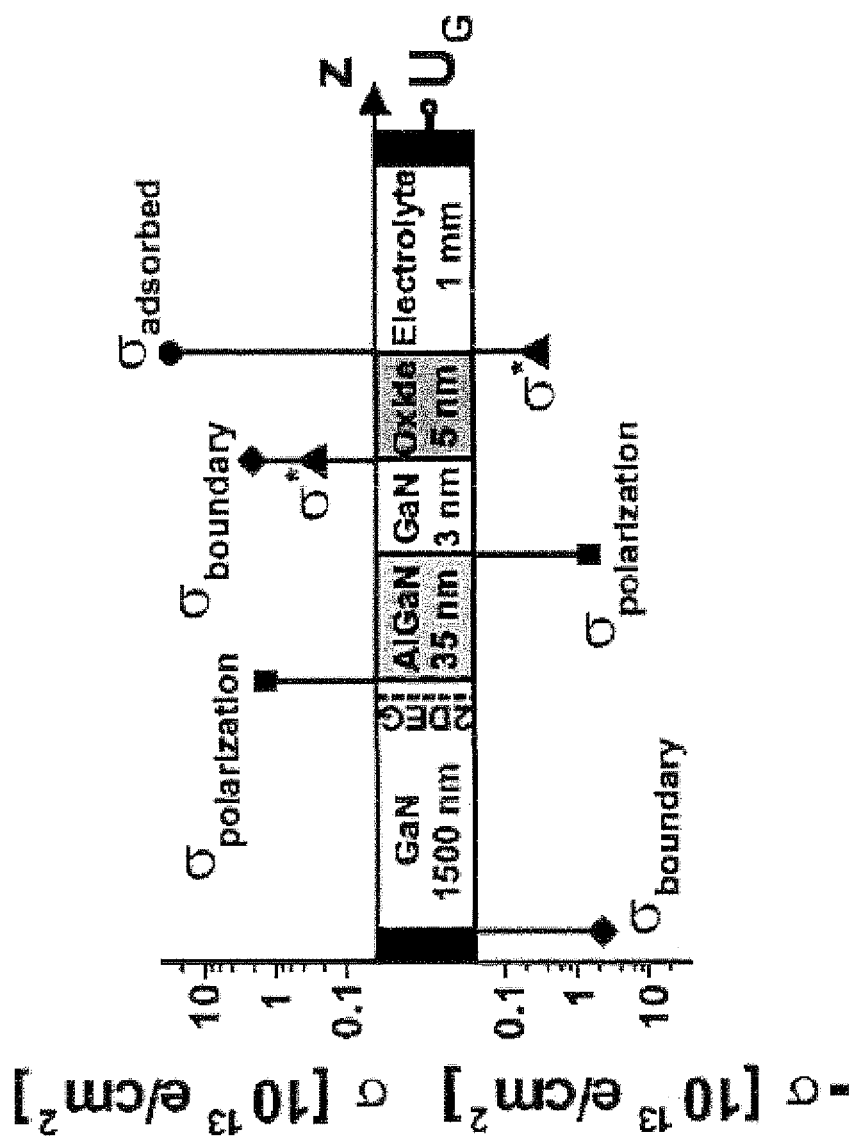
Figure 2. Charge distribution for GaN-based HFET in solution.[14]

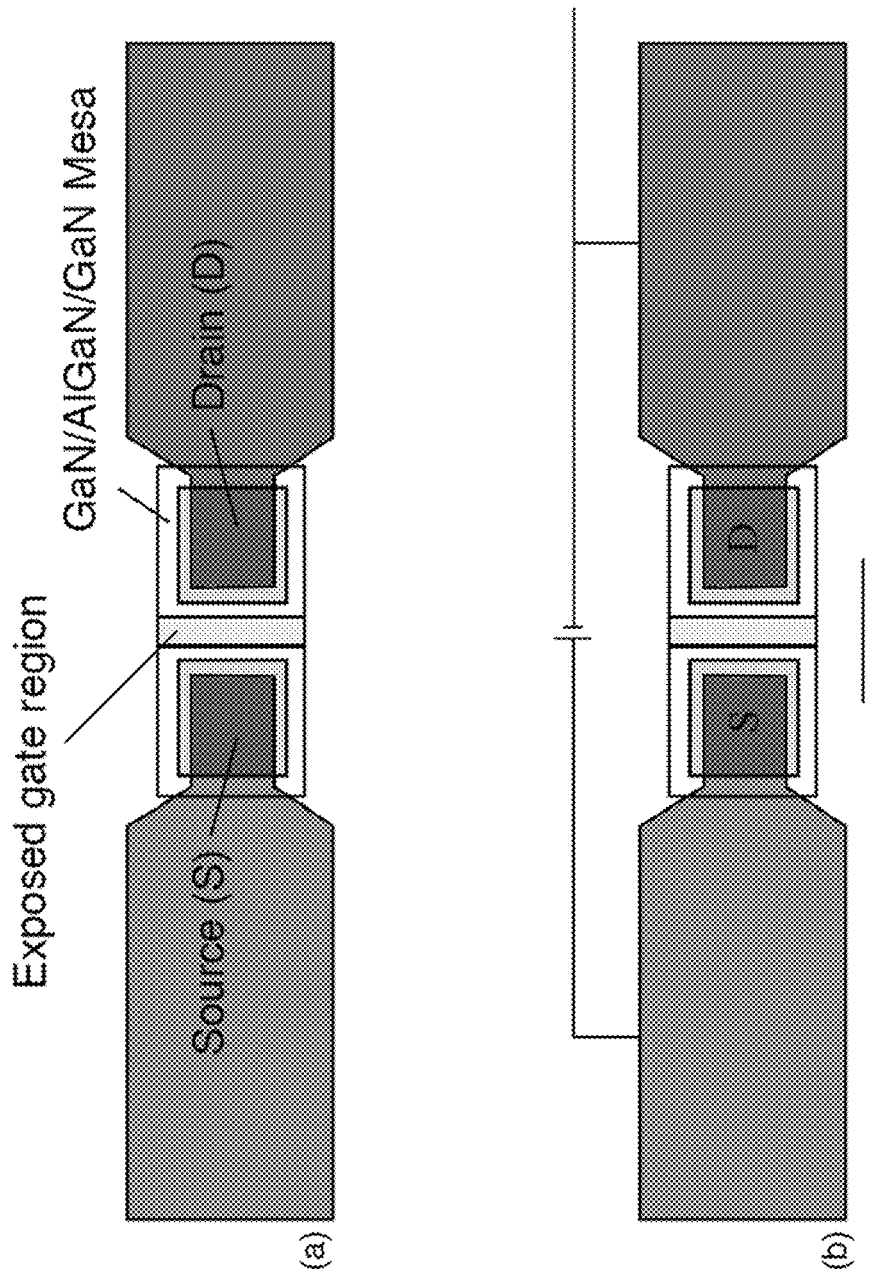
Figure 3. Schematic illustration of gateless FET

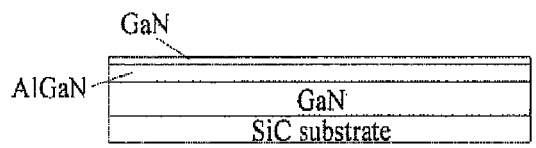 MBE growth of GaN/AlGaN/GaN

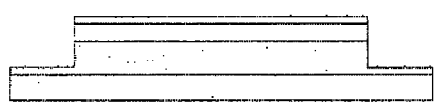 Mesa etching to define HEMT

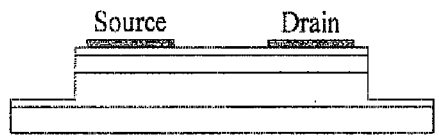 Photolithography and metallizaton of source and drain (Ti/Al/Ni/Au)

 Deposition of SiO$_2$ insulator with exposed regions over the source and drain contacts

 Photolithography and metallizaton of Au lines from the source and drain contacts (and Ag/AgCl reference electrode)

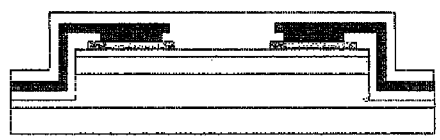 Deposition of SiO$_2$ insulator

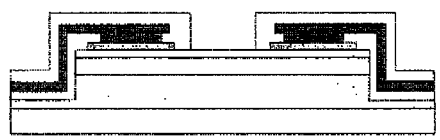 Wet plus dry etching to expose the gate region

Figure 4: Gateless FET Fabrication

GAN-BASED NITRIC OXIDE SENSORS AND METHODS OF MAKING AND USING THE SAME

CROSS REFERENCE TO RELATED APPLICATIONS

This application is a divisional of and claims priority to U.S. patent application Ser. No. 11/937,375, filed on Nov. 8, 2007, which application is based on and claims domestic priority benefits under 35 USC §119(e) from U.S. Provisional Application Ser. No. 60/857,502 filed on Nov. 8, 2006, the entire disclosures of which are hereby incorporated herein by reference.

STATEMENT REGARDING FEDERALLY SPONSORED RESEARCH

This invention was made with U.S. Government support awarded by the Office of Naval Research, Grant No. N00014-05-1-0316-P000. The United States has certain rights in this invention.

FIELD OF TECHNOLOGY

The technology herein relates generally to GaN-based nitric oxide (NO) active sensors. In preferred forms, the technology relates to GaN-based heterostructure field-effect transistors (HFETs), specifically AlGaN—GaN HFETs, with surface functional groups tailored for specificity to NO and S—NO species.

BACKGROUND OF THE TECHNOLOGY

Biological and chemical sensor systems are of great importance for monitoring medical and environmental conditions and warfare threats. While great strides have been made in sensor technology over recent years, sensors are still too large, unreliable and expensive for widespread and easy use.

Over a decade ago nitric oxide (NO) was named molecule of the year by the editors of *Science* because of its many diverse roles in the environment, biochemistry and defense-related fields. Subsequent research on NO has further enhanced interest in this molecule and important chemical processes, and revealed the need for more accurate and robust NO sensors. NO and S—NO species sensors capable of long-term, continuous operation in field environments for environmental sensor applications and in vivo for biomedical applications are of great interest. Such sensors have the potential to significantly impact treatment and diagnosis of disease and the well-being of the global environment.

The concept of a derivatized surface to promote specificity to target analytes, if engineered properly, is envisioned to minimize non-specific binding events at the sensor surface and eliminate the requirement of an analyte selective membrane. While functional groups could be chosen for selective sensing (such as detection of NO), a reduction in spurious surface chemical events would limit signal noise levels and provide greater sensitivity. Of scientific interest would be verification of specificity and reduced noise levels.

GaN-based devices are anticipated to offer greater sensitivity as an active transduction platform. HFET devices are generally characterized by a well-defined two-dimensional electron gas (2DEG) layer formed in the near region of two coincident, epitaxial semiconductors. The induced polarization at this interface for III-N heterojunctions leads to charge densities as high as $10^{13}$ cm$^{-2}$. An interesting consequence of the HFET design is the dependency of the 2DEG properties on the surface electronic or charge state. Because of this surface charge coupling III-V gateless HFET devices, including AlGaN/GaN, have been shown to be sensitive to the adsorption of molecules. The surface charge coupling is an intrinsic device property for III-N heterostructures, due to their polarization characteristics, while it is an extrinsic property of most other III-V HFETs. While this has led to concerns over electronic device instability, harnessing responses to adsorbed species has direct implications in sensor technology.

GaN has emerged in the last decade as an important semiconductor for a range of applications, from visible to UV emitters to microwave power amplifiers. In comparison to other more advanced semiconductor systems, such as Si and GaAs, GaN offers significant advantages for sensing, including its' robustness and relatively strong surface-coupled FET drain current. It is expected that functionalized surfaces of GaN-based sensors can be engineered to target almost any specific analyte for chemical or biological application.[7]

AlGaN/GaN HEMT devices have recently shown utility in sensor applications indicating these devices to be pH-responsive (⁻OH and H⁺ sensitive) and sensitive to polar liquids, including methanol, propanol, water, and acetone. Acetone showed the greatest response which was attributed to its high dipole moment. To foster selectivity to target analytes, AlGaN/GaN HFETs have been integrated with lipid bilayer membranes as well. In comparison, passivation and chemical functionalization of AlGaAs/GaAs HFET devices have been studied to promote electrical and materials stability, with recent efforts targeting biosensor applications. Interestingly, AlGaAs/GaAs HFETs have been evaluated for sensor response to NO in order to exploit its high carrier mobility (See U.S. Pat. No. 6,433,356 and US Published Patent Application No. 2004/0072360, the entire content of each being expressly incorporated hereinto by reference). U.S. Pat. No. 6,647,796 (the entire content of which is expressly incorporated hereinto by reference) discloses an integrated microsensor which includes a bowed micromachined membrane coupled to a substrate to provide a strain-FET comprised of an AlGaN/GaN heterostructure.

Covalent attachment of iron-porphyrin (Hemin) molecules to GaAs and the corresponding functionalized sensor response have also been reported. Sensitivity to 1 μM NO in physiological aqueous solutions (pH 7.4) at room temperature was observed. In addition, the functional groups were reported to enhance GaAs material stability. Yet, concerns over the presence of arsenic for biomedical sensing applications and the existence of Fermi level pinning, which masks sensing response, have been problematic. Materials stability is a major consideration in aqueous sensing environments where surface instabilities and oxide dissolution can mitigate sensor performance.

GaN's high 2DEG conductivity, extreme corrosion resistance, and strong surface state coupling to the 2DEG (with minimal Fermi level pinning) make for an ideal FET-based sensor platform. Additionally the polarization charge on the surface of the HFET can induce accelerated functionalization and allow for a wide range of molecules to be adsorbed to the surface for selective and sensitive detection of NO. This controllable surface charge distinguishes a GaN-based sensor from one that is GaAs-based. It is our intention to functionalize the GaN surface with molecular groups that offer a host of engineering options for tailorable sensing capability. Furthermore, the materials structure of the device can be designed to operate in enhancement-mode, which will allow for more contrasting detection of NO. The device could also be designed to incorporate Saville and Saville-like detection of S—NO species. This selectivity is desirable for an NO sensor if the hemin molecule can be functionalized to the GaN surface. The addition of a semi-permeable membrane such as Nafion over the gate region could also enhance the selectivity of this device by preventing molecules such as $NO_2$ from reaching the active surface layer. This would enable the device to be utilized in a variety of environments with the ability to "filter out" other possible analyte responses. Adsorbed NO by the hemin molecule has been shown to decrease the surface potential of GaAs, which caused an increase in current throughout the device. An optimized AlGaN/GaN device is expected have higher surface sensitivity than GaAs-based devices, allowing for more precise measurements and more reliable signals at lower concentrations of NO. AlGaN/GaN has roughly five times greater carrier density within the 2DEG compared to AlGaAs/GaAs HEMT devices. Interestingly, the AlGaAs/GaAs sensors have been shown to be reversible when exposed to a 10 ns 532 nm laser pulse. This visible wavelength could transmit through the backside of the GaN device because of its transparency, conceivably providing a means to periodically refresh the sensor.

SUMMARY OF THE TECHNOLOGY

According to the technology disclosed herein, GaN-based heterojunction field effect transistor (HFET) sensors are provided with engineered, functional surfaces that act as pseudo-gates, modifying the drain current upon analyte capture. The transduction platform is an active device that may be tuned for responsivity and sensitivity. NO and S—NO species play an important role in many biological processes including their relevancy to immune, antimicrobial, smooth tissue relaxant, and neuronal bioactivities. (As used herein and in the accompanying claims, the phrase "NO-species" is intended to refer to both NO per se as well as S—NO.)

NO-sensing devices in accordance with the technology disclosed herein have benefits across many research and application domains, for example from the study of chemical reactions in the biological realm to monitoring the levels of analytes in aqueous habitat environments. While silicon-based biosensors have paved the way for ideas and applications based on other materials, semiconductors with enhanced materials properties are of great interest for study and further application.

According to some aspects of the invention, a device for sensing nitric oxide (NO) species in a NO-containing fluid (e.g., liquids and gases) is provided which comprises a semiconductor structure that includes a pair of separated GaN layers and an AlGaN layer interposed between and in contact with the GaN layers. Source and drain contact regions are formed on one of the GaN layers, and an exposed GaN gate region is formed between the source and drain contact regions for contact with the NO-containing fluid. The semiconductor structure most preferably is formed on a suitable substrate (e.g., SiC).

An insulating layer may be provided so as to cover the semiconductor structure. The insulating layer will have a window formed therein so as to maintain exposure of the GaN gate region and thereby allow the gate region to contact the NO-containing fluid. Electrical contact pads are preferably provided in some embodiments so as to be in electrical contact with the source and drain contact regions, respectively. Electrical leads may thus be connected to the contact pads.

According to other embodiments, the NO detection device will include a metalloporphyrin adsorbed on the GaN gate region. If present, the metalloporphyrin is preferably a porphyrin containing as a central metal atom Fe, Co, Ni, Zn, Mk, Cu, Ru, V, Pb or Cr.

According to one presently preferred embodiment, a device is provided for the detection of nitric oxide (NO) species in response to being brought into contact with a NO-containing fluid, the device comprising a multilayer semiconductor structure which includes (i) a substrate, (ii) a GaN base layer formed on the substrate, (iii) an AlGaN layer formed on the GaN base layer, and (iv) a GaN detecting layer formed on the AlGaN layer; metallized source and drain contact regions formed on the GaN detecting layer; and electrical contact pads in electrical contact with the metallized source and drain contact regions, respectively, wherein the source and drain contact regions establish therebetween a gate region of the GaN detecting layer which is capable of being contacted by the NO-containing fluid to allow detection of the NO species therein.

According to other aspects of the invention, methods of detecting NO-species are provided which contemplate bringing a device as briefly described above into contact with a NO-containing fluid, and detecting NO-species in response to changes in adsorbed charge surface potential at the GaN gate region.

Other aspects of the invention include methods of making a device for detection of nitric oxide (NO) species in a NO-containing fluid. In this regard, the methods preferably comprise the steps of (a) forming a multilayer semiconductor structure to sequentially include a GaN base layer formed on the substrate, an AlGaN layer formed on the GaN base layer, and a GaN detecting layer formed on the AlGaN layer; (b) forming metallized source and drain contact regions on the GaN detecting layer and to establish therebetween a gate region of the GaN detecting layer which is capable of being contacted by the NO-containing fluid to allow detection of the NO species therein; and (c) forming electrical contact pads in electrical contact with the metallized source and drain contact regions, respectively.

These and other features and advantages will be better and more completely understood by referring to the following detailed description of exemplary non-limiting illustrative embodiments in conjunction with the drawings

BRIEF DESCRIPTION OF THE DRAWINGS

The accompanying drawings further illustrate the technology disclosed herein, in which:

FIG. 1 is a schematic of an exemplary illustrative non-limiting functionalized GaN—AlGaN HFET;

FIG. 2 is an exemplary non-limiting illustration of charge distribution for GaN-based HFET in solution;

FIG. 3 is a conceptual illustration of an exemplary illustrative non-limiting gateless FET design; and FIG. 4 is an exemplary illustrative non-limiting gateless FET design.

DETAILED DESCRIPTION

A cross-section of the HFET structure in accordance with the technology disclosed herein is shown in FIG. 1, with a conceptual view of the NO sensing via the hemin molecule. In this regard, it should be noted that the benzoic acid molecule acts as a spacer for the hemin molecules to prevent polymerization without obstruction of the Fe binding site on hemin to NO.

The effective operation of the GaN sensor requires design and optimization of the heterostructure layer. The charge distribution of an AlGaN—GaN HFET sensor exposed to an electrolyte is shown in FIG. 2. The potential at the device surface in such a structure establishes the potential throughout the structure as the boundary condition. The sensing mechanism rests upon changes in the adsorbed charge and the surface potential. The change in charge can be understood to be exactly as stated: Absorption of analyte onto the surface or a modification of the charge environment on or near the surface, such as the molecular dipole moment change upon NO binding. Recent work by Bayer, et. al.[14] shows that modeling can be used to maximize the sensitivity of the structure to surface charge perturbations. Furthermore this sensor design could be readily incorporated with a reference electrode and a counter electrode for electrochemical detection of NO, operating similarly to an ion-selective FET (ISFET).

It is important to point out that the sensitivity is strongly dependent upon the distance between the adsorbed charge and the 2DEG. For example, in FIG. 2 discussed above a leaky oxide allows charge to migrate closer to the channel and hence sensitivity is increased. In addition, it has been found that a N-polar device is preferred if ideal due to the ability to place the 2DEG within a few 10s of nm from the surface. In this case, the 2DEG concentration is changed from $1-10\times 10^{12}$ $cm^{-2}$ for a change of $40\times 10^{13}$ $cm^{-2}$ surface charge change. Layers above the 2DEG are therefore provided to enhance the coupling between surface charge and potential modification and 2DEG change. Since a metal gate is not used in accordance with the devices embodying the invention, layer designs allow for more complex structures to peak fields near the surface and maximize the sensitivity.

In addition the surface electronic state perturbation may be enhanced through the choice of specific functional group. One approach is simply to explore different porphyrin species, preferably metalloporphyrins, such as porphyrins containing as a central metal atom Fe, co, Ni, Zn, Mk, Cu, Ru, V, Pb or Cr. Such metalloporphyrins may be adsorbed onto the surface of the GaN gate region to enhance selective detection of NO. For example, it is known that Ni and Fe porphyrins have the highest sensitivities to NO. This high sensitivity could reduce other analyte detection to noise, allowing for the selective detection of NO. Selectivity could also be enhanced with integrated sensors that target other analytes that would be expected in a given system (to filter out that signal from NO).

One can consider the inorganic-organic interface between the semiconductor and the porphyrin group via a frontier molecular orbital model The attached molecule is engineered from two perspectives—the surface binding group facilitates the electronic and chemical interaction between the molecule and surface, and the headgroup, in this case the porphyrin, is engineered for analyte capture and identification. The work function of the semiconductor surface changes due to the dipole moment of the molecule via an electron affinity change or band-bending change or both. These effects can be examined through combinations of FTIR (Fourier Transform Infrared spectroscopy) for characterizing bonding, EFM (electron force microscopy) to measure work function, and surface photovoltage to determine the role of band-bending in surface electronic changes. The electron affinity is directly modified by dipoles on the surface with changes correlated to the dipole moment. Changes in the work function depend on dipole moment, surface coverage of molecules and tilt of molecules relative to the semiconductor surface. The band-bending is governed by net charge density and the position and density of surface states. We will explore the band line-ups of the surface layers and the molecular orbitals and optimize for maximized electronic coupling between the molecule and the semiconductor.

AlGaN/GaN HEMT structures may advantageously be deposited using rf plasma assisted molecular beam epitaxy (MBE). Mesa-etching may be used to electrically isolate sensor devices. Subsequent source-drain contact metallizations (Ti/Al/Ni/Au) may be deposited through photolithography. And, a passivation layer may be deposited followed by patterned Au leads extending to the edge of the substrate for wire-bonding to a printed circuit board. A passivation overlayer may finally be deposited, and the gate region exposed through a combination of dry and wet etching. FIG. 3 shows a schematic cross-section and plan view image of an AlGaN/GaN HEMT sensor embodying the present invention.

FIG. 4 shows a plan view image of an AlGaN/GaN HEMT sensor and the corresponding process flow diagram for microfabricating such devices. As depicted, a GaN layer is deposited on a suitable substrate (SiC) by MBE techniques, followed successively by MBE deposition of an AlGaN layer and a GaN layer. The resulting structure is mesa etched to define a HEMT. Photolithography and metallization of source and drain regions (Ti/Al/Ni/Au) may then be fabricated onto desired locations of the GaN layer.

A layer of a $SiO_2$ insulator may then be applied over the structure. The insulator layer is provided with exposed regions over the source and drain contacts. Subsequent photolithography and metallization of metal (preferably Au) establish metal contact pads and leads from the source and drain contacts (and Ag/AgCl reference electrode). A final insulator layer (e.g., of $SiO_2$) is thereafter deposited over the metallized leads. The final insulator layer is then etched (e.g., using conventional we and dry etching techniques) so as to expose a gate region of the GaN layer.

The thus fabricated device may then be operatively associated with a system to provide sensing of NO and/or S—NO analyte species. That is, the fabricated device may be brought into contact with a fluid source containing NO and/or S—NO to allow detection of the same.

While the technology herein has been described in connection with exemplary illustrative non-limiting implementations, the invention is not to be limited by the disclosure. The invention is intended to be defined by the claims and to cover all corresponding and equivalent arrangements whether or not specifically disclosed herein.

CITATIONS[1]

[1] Each of the publications cited below is expressly incorporated in its entirety herein.

1. Eickhoff, M., J. Schalwig, G. Steinhoff, O. Weidemann, L. Gorgens, R. Neuberger, M. Hermann, B. Baur, G. Muller, O. Ambacher, and M. Stutzmann, *Electronics and sensors based on pyroelectric AlGaN/GaN heterostructures; Part B: Sensor applications*. Phys. Stat. Sol. (c), 2003. 0(6): p. 1908.
2. Skromme, B. J., C. J. Sandroff, E. Yablonovitch, and T. Gmitter, *Effects of passivating ionic films on the photoluminescence properties of GaAs*. Appl. Phys. Lett., 1987. 51(24): p. 2022.
3. Gomez, R., N. Noguera, A. Ivorra, R. Villa, and J. Millan, *Instrumentation system for in vivo organ studies*. IEEE CNF, 2001. 1: p. 264.
4. Haga, Y. and M. Esashi, *Biomedical microsystems for minimally invasive diagnosis and treatment*. Proc. of IEEE, 2004. 92: p. 98.

5. Gaston, B., *Nitric oxide and thiol groups*. Biochim. Biophys. Acta., 1999. 1411: p. 323.
6. Culotta, E. and D. E. Koshland, *NO News is Good News*. Science, 1992. 258(5090): p. 1862.
7. Pearton, S. J., B. S. Kang, S. Kim, and F. Ren, *GaN-based diodes and transistors for chemical, gas, biological and pressure sensing*. J. Phys.: Condens. Matter, 2004. 16: p. R961.
8. Steinhoff, G., M. Hermann, W. J. Schaff, L. F. Eastman, M. Stutzmann, and M. Eickhoff, *pH response of GaN surfaces and its application for pH-sensitive field-effect transistors*. Appl. Phys. Lett., 2003. 83(1): p. 177.
9. Stutzmann, M., G. Steinhoff, and M. Eickhoff, *GaN-based heterostructures for sensor applications*. Dia. Related Mat., 2002. 11: p. 886.
10. Gartsman, K., D. Cahen, A. Kadyshevitch, J. Libman, T. Moav, R. Naaman, A. Shanzer, V. Umansky, and A. Vilan, *Molecular control of a GaAs transistor*. Chem. Phys. Let., 1998. 283(5): p. 301.
11. Kirchner, C., M. George, B. Stein, W. J. Parak, H. E. Gaub, and M. Seitz, *Corrosion protection and long-term chemical functionalization of gallium arsenide in an aqueous environment*. Adv. Funct. Mater., 2002. 12(4): p. 266.
12. Wu, D. G., D. Cahen, P. Graf, R. Naaman, A. Nitzan, and D. Shvarts, *Direct Detection of Low-Concentration NO in Physiological Solutions by a New GaAs-Based Sensor*. Chem. Eur. J., 2001. 7(8): p. 1743.
13. Rovira, C., K. Kunc, J. Flutter, P. Ballone, and M. Parrinello, *Equilibrium Geometries and Electronic Structure of Iron-Porphyrin Complexes: A Density Functional Study*. J. Phys. Chem. A, 1997. 101: p. 8914.
14. Bayer, M., C. Uhl, and P. Vogl, *Theoretical study of electrolyte gate AlGaN/GaN field effect transistors*. Appl. Phys. Lett., 2005. 97: p. 033703.
15. Kadish, K. M., K. M. Smith, and R. Guilard, eds. *Applications: Past, Present and Future*. The Porphyrin Handbook. Vol. 6. 1999, Academic Press: San Diego. 240-250.
16. Ashkenasy, G., D. Cahen, R. Cohen, A. Shanzer, and A. Vilan, *Molecular Engineering of Semiconductor Surfaces and Devices*. Acc. Chem. Res., 2002. 35: p. 121.

The invention claimed is:

1. A method of making a device for detection of nitric oxide (NO) species in a NO-containing fluid, the method comprising the steps of:
   (a) forming a multilayer semiconductor structure to sequentially include a GaN base layer formed on the substrate, an AlGaN layer formed on the GaN base layer, and a GaN detecting layer formed on the AlGaN layer;
   (b) forming metallized source and drain contact regions on the GaN detecting layer and to establish therebetween a gate region of the GaN detecting layer which is capable of being contacted by the NO-containing fluid to allow detection of the NO species therein;
   (c) forming electrical contact pads in electrical contact with the metallized source and drain contact regions, respectively; and
   (d) derivitizing the GaN gate region with a porphyrin.

2. A method as in claim 1, wherein step (a) includes forming the multilayer semiconductor structure on a substrate.

3. A method as in claim 1, further comprising covering the semiconductor structure with an insulating layer, and forming a window in the semiconductor structure so as to maintain exposure of the GaN gate region for contact with the NO-containing fluid.

4. A method as in claim 1, further comprising forming electrical leads connected to the contact pads.

5. A method as in claim 1, wherein the porphyrin is a metalloporphyrin.

6. A method as in claim 5, wherein the metalloporphyrin is a porphyrin containing as a central metal atom Fe, Co, Ni, Zn, Mn, Cu, Ru, V, Pb or Cr.

* * * * *